(12) United States Patent
Cabiri

(10) Patent No.: US 8,465,455 B2
(45) Date of Patent: *Jun. 18, 2013

(54) CARTRIDGE INSERTION ASSEMBLY

(75) Inventor: Oz Cabiri, Macabim (IL)

(73) Assignee: Medimop Medical Projects Ltd., Ra'anana (IL)

(*) Notice: Subject to any disclaimer, the term of this patent is extended or adjusted under 35 U.S.C. 154(b) by 0 days.

This patent is subject to a terminal disclaimer.

(21) Appl. No.: 13/272,555

(22) Filed: Oct. 13, 2011

(65) Prior Publication Data

US 2012/0035546 A1 Feb. 9, 2012

Related U.S. Application Data

(63) Continuation of application No. 12/559,563, filed on Sep. 15, 2009, now Pat. No. 8,157,769.

(51) Int. Cl.
*A61M 1/00* (2006.01)
*A61M 37/00* (2006.01)

(52) U.S. Cl.
USPC .......................................... 604/154; 604/151

(58) Field of Classification Search
USPC ............. 604/890.1, 48, 93.01, 131, 151, 152, 604/154, 155, 246, 257
See application file for complete search history.

(56) References Cited

U.S. PATENT DOCUMENTS

| | | | |
|---|---|---|---|
| 1,795,630 A | 3/1931 | Wilson | |
| 3,212,685 A | 10/1965 | Swan et al. | |
| 3,794,028 A | 2/1974 | Mueller et al. | |
| 4,195,636 A | 4/1980 | Behnke | |
| 4,300,554 A | 11/1981 | Hessberg et al. | |
| 4,403,987 A | 9/1983 | Gottinger | |
| 4,435,173 A | 3/1984 | Siposs et al. | |
| 4,599,082 A | 7/1986 | Grimard | |
| 4,867,743 A | 9/1989 | Vaillancourt | |
| 4,886,499 A | 12/1989 | Cirelli et al. | |
| 4,929,241 A | 5/1990 | Kulli | |
| 5,109,850 A | 5/1992 | Blanco et al. | |
| 5,190,521 A | 3/1993 | Hubbard et al. | |
| 5,300,045 A | 4/1994 | Plassche, Jr. | |

(Continued)

FOREIGN PATENT DOCUMENTS

| | | |
|---|---|---|
| WO | 9307922 A1 | 4/1993 |
| WO | 9407553 A1 | 4/1994 |

(Continued)

OTHER PUBLICATIONS

Copaxone®, Manufactured by Teva Pharmaceutical Industries Ltd.

(Continued)

*Primary Examiner* — Victoria P Shumate
*Assistant Examiner* — Leah Stohr
(74) *Attorney, Agent, or Firm* — Panitch Schwarze Belisario & Nadel LLP

(57) ABSTRACT

A cartridge insertion assembly including apparatus with a pathway formed therein, a cartridge insertable into the pathway, the cartridge including a cartridge coupling element connectable to an activation mechanism disposed in the apparatus operative to cause a substance contained in the cartridge to be metered out of the cartridge, and a door pivoted to the apparatus that includes a door coupling element arranged with respect to the cartridge such that when the door is in a fully closed position, the door coupling element couples the cartridge coupling element with a coupling element of the activation mechanism.

17 Claims, 11 Drawing Sheets

U.S. PATENT DOCUMENTS

| | | | |
|---|---|---|---|
| 5,366,498 A | 11/1994 | Brannan et al. | |
| 5,383,865 A | 1/1995 | Michel | |
| 5,478,315 A | 12/1995 | Brothers et al. | |
| 5,482,446 A | 1/1996 | Williamson et al. | |
| 5,505,709 A * | 4/1996 | Funderburk et al. | 604/155 |
| 5,593,390 A | 1/1997 | Castellano et al. | |
| 5,616,132 A | 4/1997 | Newman | |
| 5,643,218 A | 7/1997 | Lynn et al. | |
| 5,645,955 A | 7/1997 | Maglica | |
| 5,662,678 A | 9/1997 | Macklin | |
| 5,690,618 A | 11/1997 | Smith et al. | |
| 5,766,186 A | 6/1998 | Faraz et al. | |
| 5,795,675 A | 8/1998 | Maglica | |
| 5,800,420 A | 9/1998 | Gross et al. | |
| 5,807,375 A | 9/1998 | Gross et al. | |
| 5,814,020 A | 9/1998 | Gross | |
| 5,836,920 A | 11/1998 | Robertson | |
| 5,851,197 A | 12/1998 | Marano et al. | |
| 5,858,001 A | 1/1999 | Tsals et al. | |
| 5,931,814 A | 8/1999 | Alex et al. | |
| 5,948,392 A | 9/1999 | Haslwanter et al. | |
| 5,954,697 A | 9/1999 | Srisathapat et al. | |
| 5,957,895 A | 9/1999 | Sage et al. | |
| 5,968,011 A | 10/1999 | Larsen et al. | |
| 6,074,369 A | 6/2000 | Sage et al. | |
| 6,186,982 B1 | 2/2001 | Gross et al. | |
| 6,200,289 B1 | 3/2001 | Hochman et al. | |
| 6,200,296 B1 | 3/2001 | Dibiasi et al. | |
| 6,224,569 B1 | 5/2001 | Brimhall | |
| 6,277,098 B1 | 8/2001 | Klitmose et al. | |
| 6,277,099 B1 | 8/2001 | Strowe et al. | |
| 6,287,283 B1 | 9/2001 | Ljunggreen et al. | |
| 6,336,729 B1 | 1/2002 | Pavelle et al. | |
| 6,391,005 B1 | 5/2002 | Lum et al. | |
| 6,485,461 B1 | 11/2002 | Mason et al. | |
| 6,500,150 B1 | 12/2002 | Gross et al. | |
| 6,503,231 B1 | 1/2003 | Prausnitz et al. | |
| 6,517,517 B1 | 2/2003 | Farrugia et al. | |
| 6,558,351 B1 | 5/2003 | Steil et al. | |
| 6,589,229 B1 | 7/2003 | Connelly et al. | |
| 6,595,956 B1 | 7/2003 | Gross et al. | |
| 6,645,181 B1 | 11/2003 | Lavi et al. | |
| 6,652,482 B2 | 11/2003 | Hochman | |
| 6,656,158 B2 | 12/2003 | Mahoney et al. | |
| 6,656,159 B2 | 12/2003 | Flaherty | |
| 6,689,118 B2 | 2/2004 | Alchas et al. | |
| 6,699,218 B2 | 3/2004 | Flaherty et al. | |
| 6,743,211 B1 | 6/2004 | Prausnitz et al. | |
| 6,749,587 B2 | 6/2004 | Flaherty | |
| 6,768,425 B2 | 7/2004 | Flaherty et al. | |
| 6,786,890 B2 | 9/2004 | Preuthun et al. | |
| 6,800,071 B1 | 10/2004 | McConnell et al. | |
| 6,805,687 B2 | 10/2004 | Dextradeur et al. | |
| 6,824,529 B2 | 11/2004 | Gross et al. | |
| 6,843,782 B2 | 1/2005 | Gross et al. | |
| 6,854,620 B2 | 2/2005 | Ramey | |
| 6,905,298 B1 | 6/2005 | Haring | |
| 6,960,192 B1 | 11/2005 | Flaherty et al. | |
| 7,001,360 B2 | 2/2006 | Veasey et al. | |
| 7,060,054 B2 | 6/2006 | Nissels | |
| 7,060,059 B2 | 6/2006 | Keith et al. | |
| 7,128,727 B2 | 10/2006 | Flaherty et al. | |
| 7,144,384 B2 | 12/2006 | Gorman et al. | |
| 7,247,149 B2 | 7/2007 | Beyerlein | |
| 7,250,037 B2 | 7/2007 | Shermer et al. | |
| 7,291,159 B2 | 11/2007 | Schmelzeisen-Redeker et al. | |
| 7,303,549 B2 | 12/2007 | Flaherty et al. | |
| 7,364,570 B2 | 4/2008 | Gerondale et al. | |
| 7,390,314 B2 | 6/2008 | Stutz, Jr. et al. | |
| 7,407,493 B2 | 8/2008 | Cane' | |
| 7,455,663 B2 | 11/2008 | Bikovsky | |
| 7,530,964 B2 | 5/2009 | Lavi et al. | |
| 7,565,208 B2 | 7/2009 | Harris et al. | |
| 7,569,050 B2 | 8/2009 | Moberg et al. | |
| 7,585,287 B2 | 9/2009 | Bresina et al. | |
| 7,588,559 B2 | 9/2009 | Aravena et al. | |
| 7,628,770 B2 | 12/2009 | Ethelfeld | |
| 7,637,891 B2 | 12/2009 | Wall | |
| 7,641,649 B2 | 1/2010 | Moberg et al. | |
| 7,678,079 B2 | 3/2010 | Shermer et al. | |
| 7,686,787 B2 | 3/2010 | Moberg et al. | |
| 7,699,829 B2 | 4/2010 | Harris et al. | |
| 7,713,238 B2 | 5/2010 | Mernoe | |
| 7,744,589 B2 | 6/2010 | Mounce et al. | |
| 7,749,194 B2 | 7/2010 | Edwards et al. | |
| 7,806,868 B2 * | 10/2010 | De Polo et al. | 604/155 |
| 7,854,723 B2 | 12/2010 | Hwang et al. | |
| 7,967,795 B1 | 6/2011 | Cabiri | |
| 8,057,431 B2 | 11/2011 | Woehr et al. | |
| 8,086,306 B2 | 12/2011 | Katzman et al. | |
| 8,323,250 B2 | 12/2012 | Chong et al. | |
| 2001/0025168 A1 | 9/2001 | Gross et al. | |
| 2001/0041869 A1 | 11/2001 | Causey et al. | |
| 2002/0010423 A1 | 1/2002 | Gross et al. | |
| 2002/0040208 A1 | 4/2002 | Flaherty et al. | |
| 2002/0055711 A1 | 5/2002 | Lavi et al. | |
| 2002/0123740 A1 | 9/2002 | Flaherty et al. | |
| 2002/0169215 A1 | 11/2002 | Meng | |
| 2003/0009133 A1 | 1/2003 | Ramey | |
| 2003/0135159 A1 | 7/2003 | Daily et al. | |
| 2003/0171717 A1 | 9/2003 | Farrugia et al. | |
| 2004/0010207 A1 | 1/2004 | Flaherty et al. | |
| 2004/0092873 A1 | 5/2004 | Moberg | |
| 2004/0127857 A1 | 7/2004 | Shemesh et al. | |
| 2004/0186419 A1 | 9/2004 | Cho | |
| 2004/0260233 A1 | 12/2004 | Garibotto et al. | |
| 2005/0033234 A1 | 2/2005 | Sadowski et al. | |
| 2005/0065466 A1 | 3/2005 | Vedrine | |
| 2005/0065472 A1 | 3/2005 | Cindrich et al. | |
| 2005/0171512 A1 | 8/2005 | Flaherty | |
| 2005/0197650 A1 | 9/2005 | Sugimoto et al. | |
| 2005/0203461 A1 | 9/2005 | Flaherty et al. | |
| 2005/0238507 A1 | 10/2005 | Dilanni et al. | |
| 2005/0283114 A1 | 12/2005 | Bresina et al. | |
| 2006/0095014 A1 | 5/2006 | Ethelfeld | |
| 2006/0122577 A1 | 6/2006 | Poulsen et al. | |
| 2006/0173406 A1 | 8/2006 | Hayes et al. | |
| 2006/0173439 A1 | 8/2006 | Thorne et al. | |
| 2006/0211982 A1 | 9/2006 | Prestrelski et al. | |
| 2006/0229569 A1 | 10/2006 | Lavi et al. | |
| 2006/0264889 A1 | 11/2006 | Moberg et al. | |
| 2006/0264890 A1 | 11/2006 | Moberg et al. | |
| 2006/0264894 A1 | 11/2006 | Moberg et al. | |
| 2006/0283465 A1 | 12/2006 | Nickel et al. | |
| 2006/0293722 A1 | 12/2006 | Slatkine et al. | |
| 2007/0021733 A1 | 1/2007 | Hansen et al. | |
| 2007/0049865 A1 | 3/2007 | Radmer et al. | |
| 2007/0073228 A1 | 3/2007 | Mernoe et al. | |
| 2007/0118405 A1 | 5/2007 | Campbell et al. | |
| 2007/0167912 A1 * | 7/2007 | Causey et al. | 604/131 |
| 2007/0185449 A1 | 8/2007 | Mernoe | |
| 2007/0197968 A1 | 8/2007 | Pongpairochana et al. | |
| 2007/0203454 A1 | 8/2007 | Shermer et al. | |
| 2007/0233038 A1 | 10/2007 | Pruitt et al. | |
| 2008/0021439 A1 | 1/2008 | Brittingham et al. | |
| 2008/0033367 A1 | 2/2008 | Haury et al. | |
| 2008/0033369 A1 | 2/2008 | Kohlbrenner et al. | |
| 2008/0051711 A1 | 2/2008 | Mounce et al. | |
| 2008/0051730 A1 | 2/2008 | Bikovsky | |
| 2008/0059133 A1 | 3/2008 | Edwards et al. | |
| 2008/0097381 A1 | 4/2008 | Moberg et al. | |
| 2008/0108951 A1 | 5/2008 | Jerde et al. | |
| 2008/0140006 A1 | 6/2008 | Eskuri et al. | |
| 2008/0140018 A1 | 6/2008 | Enggaard et al. | |
| 2008/0188813 A1 | 8/2008 | Miller et al. | |
| 2008/0208138 A1 | 8/2008 | Lim et al. | |
| 2008/0215006 A1 | 9/2008 | Thorkild | |
| 2008/0262436 A1 | 10/2008 | Olson | |
| 2008/0269723 A1 | 10/2008 | Mastrototaro et al. | |
| 2008/0294143 A1 | 11/2008 | Tanaka et al. | |
| 2008/0306449 A1 | 12/2008 | Kristensen et al. | |
| 2008/0312601 A1 | 12/2008 | Cane | |
| 2008/0319416 A1 | 12/2008 | Yodfat et al. | |
| 2009/0041805 A1 | 2/2009 | Walker | |
| 2009/0048347 A1 | 2/2009 | Cohen et al. | |
| 2009/0054750 A1 | 2/2009 | Jennewine | |
| 2009/0069784 A1 | 3/2009 | Estes et al. | |

| | | | |
|---|---|---|---|
| 2009/0088731 A1 | 4/2009 | Campbell et al. | |
| 2009/0093792 A1 | 4/2009 | Gross et al. | |
| 2009/0093793 A1 | 4/2009 | Gross et al. | |
| 2009/0105650 A1* | 4/2009 | Wiegel et al. | 604/152 |
| 2009/0124977 A1 | 5/2009 | Jensen | |
| 2009/0143735 A1 | 6/2009 | De Polo et al. | |
| 2009/0149830 A1 | 6/2009 | Spector | |
| 2009/0182277 A1 | 7/2009 | Carter | |
| 2009/0234319 A1 | 9/2009 | Marksteiner | |
| 2009/0240240 A1 | 9/2009 | Hines et al. | |
| 2009/0253973 A1 | 10/2009 | Bashan et al. | |
| 2009/0259176 A1 | 10/2009 | Yairi | |
| 2009/0326509 A1 | 12/2009 | Muse et al. | |
| 2010/0030198 A1 | 2/2010 | Beebe et al. | |
| 2010/0057057 A1 | 3/2010 | Hayter et al. | |
| 2010/0076412 A1 | 3/2010 | Rush et al. | |
| 2010/0094255 A1 | 4/2010 | Nycz et al. | |
| 2010/0100076 A1 | 4/2010 | Rush et al. | |
| 2010/0100077 A1 | 4/2010 | Rush et al. | |
| 2010/0106098 A1 | 4/2010 | Atterbury et al. | |
| 2010/0121314 A1 | 5/2010 | Iobbi | |
| 2010/0145303 A1 | 6/2010 | Yodfat et al. | |
| 2010/0145305 A1 | 6/2010 | Alon | |
| 2010/0162548 A1 | 7/2010 | Leidig | |
| 2010/0168683 A1 | 7/2010 | Cabiri | |
| 2010/0204657 A1 | 8/2010 | Yodfat et al. | |
| 2010/0234767 A1 | 9/2010 | Sarstedt | |
| 2010/0234830 A1 | 9/2010 | Straessler et al. | |
| 2010/0274112 A1 | 10/2010 | Hoss et al. | |
| 2010/0274192 A1 | 10/2010 | Mernoe | |
| 2010/0280499 A1 | 11/2010 | Yodfat et al. | |
| 2011/0066131 A1 | 3/2011 | Cabiri | |
| 2011/0172745 A1 | 7/2011 | Na et al. | |
| 2011/0178463 A1 | 7/2011 | Cabiri | |
| 2011/0178472 A1 | 7/2011 | Cabiri | |
| 2011/0282296 A1 | 11/2011 | Harms et al. | |

FOREIGN PATENT DOCUMENTS

| | | |
|---|---|---|
| WO | 0187384 A1 | 11/2001 |
| WO | 0202165 A2 | 1/2002 |
| WO | 2006037434 A1 | 4/2006 |
| WO | 2006069380 A1 | 6/2006 |
| WO | 2006102676 A1 | 9/2006 |
| WO | 2007051563 A1 | 5/2007 |
| WO | 2008001377 A2 | 1/2008 |
| WO | 2008014908 A1 | 2/2008 |
| WO | 2008057976 A2 | 5/2008 |
| WO | 2008072229 A2 | 6/2008 |
| WO | 2009044401 | 4/2009 |
| WO | 2010078227 A1 | 7/2010 |
| WO | 2011090955 A1 | 7/2011 |

OTHER PUBLICATIONS

Daikyo Crystal Zenith® polymer, Manufactured by Daikyo Seiko, Ltd.
Int'l Preliminary Report on Patentability issued Apr. 7, 2010 in Int'l Application No. PCT/IL2008/001312; Written Opinion.
Int'l Preliminary Report on Patentability issued Sep. 1, 2011 in Int'l Application No. PCT/US2010/048556.
Int'l Search Report issued Jan. 12, 2011 in Int'l Application No. PCT/US2010/048556; Written Opinion.
Int'l Search Report issued Apr. 26, 2010 in Int'l Application No. PCT/US2009/069552.
Int'l Search Report issued May 13, 2009 in Int'l Application No. PCT/IL2008/001312.
International Preliminary Report on Patentability issued on Jul. 5, 2011 in International Application No. PCT/US2009/069552; Written Opinion.
Office Action issued Apr. 5, 2010 in U.S. Appl. No. 12/244,666.
Office Action issued Apr. 5, 2010 in U.S. Appl. No. 12/244,688.
Office Action issued Jul. 13, 2011 in U.S. Appl. No. 12/559,563.
Office Action issued Sep. 2, 2010 in U.S. Appl. No. 12/244,688.
Office Action issued Sep. 21, 2010 in U.S. Appl. No. 12/244,666.
Office Action issued Sep. 30, 2010 in U.S. Appl. No. 12/689,250.
Office Action issued Sep. 6, 2011 in U.S. Appl. No. 12/345,818.
Office Action issued Feb. 21, 2012 in U.S. Appl. No. 12/689,249.
Int'l Search Report issued Jun. 17, 2011 in Int'l Application No. PCT/US2011/021604.
Int'l Search Report issued Oct. 12, 2011 in Int'l Application No. PCT/US2011/021605.
Office Action issued Oct. 28, 2011 in U.S. Appl. No. 12/615,828.
Int'l Search Report issued Sep. 22, 2011 in Int'l Application No. PCT/IL11/00368; Written Opinion.
Int'l Preliminary Report on Patentability issued Aug. 2, 2012 in Int'l Application No. PCT/US2011/021604.
U.S. Appl. No. 13/643,470 by Alon, filed Oct. 25, 2012.
U.S. Appl. No. 13/733,516 by Cabiri, filed Jan. 3, 2013.
U.S. Appl. No. 13/521,181 by Cabiri, filed Jul. 9, 2012.
U.S. Appl. No. 13/521,167 by Cabiri, filed Jul. 9, 2012.
Office Action issued May 16, 2012 in U.S. Appl. No. 12/615,828.
Office Action issued May 3, 2012 in CN Application No. 200880117084.X.
U.S. Appl. No. 13/472,112 by Cabiri, filed May 15, 2012.
U.S. Appl. No. 13/429,840 by Cabiri, filed Mar. 26, 2012.

* cited by examiner

CARTRIDGE INSERTION ASSEMBLY

CROSS-REFERENCE TO RELATED APPLICATIONS

This present application is a continuation of U.S. application Ser. No. 12/559,563, filed on Sep. 15, 2009 and entitled "CARTRIDGE INSERTION ASSEMBLY FOR DRUG DELIVERY SYSTEM."

BACKGROUND OF THE INVENTION

The present invention generally relates to drug delivery systems, e.g., external drug pumps, and particularly to an assembly for inserting a cartridge, which contains a substance to be administered to a patient, into the drug delivery system.

External drug pumps are typically used to deliver to patients substances which contain large molecules which cannot be digested when administered orally, such as insulin. Typically, the pump is adhered to the abdomen or chest or other of the patient and delivers the substance to the patient via a cannula that is inserted into the patient subcutaneously, although the invention described below is not limited to needle administration of substances.

BRIEF SUMMARY OF THE INVENTION

The present invention seeks to provide an improved assembly for inserting a cartridge, which contains a substance to be administered to a patient, into a drug pump (or any kind of drug delivery system), as is described more in detail hereinbelow. It is noted that the term "cartridge" encompasses any kind of reservoir or container (disposable or not) for a substance that is to be administered to a patient, such as but not limited to, a vial, ampoule, bottle, pre-filled syringe and the like, and is not limited to any size or shape.

There is thus provided in accordance with an embodiment of the present invention a cartridge insertion assembly including apparatus with a pathway formed therein, a cartridge insertable into the pathway, the cartridge including a cartridge coupling element connectable to an activation mechanism disposed in the apparatus operative to cause a substance contained in the cartridge to be metered out of the cartridge, and a door pivoted to the apparatus that includes a door coupling element arranged with respect to the cartridge such that when the door is in a fully closed position, the door coupling element couples the cartridge coupling element with a coupling element of the activation mechanism.

In accordance with an embodiment of the present invention a locking latch is cantilevered from a base of the apparatus, wherein when the cartridge is fully inserted in the apparatus, the locking latch abuts against a rim of the cartridge, thereby locking the cartridge in the pathway.

In accordance with an embodiment of the present invention when the cartridge is fully inserted in the apparatus, the cartridge abuts against a cartridge stopper disposed in the apparatus.

In accordance with an embodiment of the present invention the cartridge includes a septum at an end opposite to the cartridge coupling element, and the apparatus includes a hollow needle, wherein when the cartridge is fully inserted in the apparatus, the needle punctures the septum.

In accordance with an embodiment of the present invention the door includes a closure member on an inside surface thereof, the closure member including one or more inclined ramp members, wherein closing the door causes the ramp members to slide and push against the cartridge coupling element so as to push the cartridge fully into the apparatus.

In accordance with an embodiment of the present invention the door is formed with one or more ribs, which when the door is fully closed, the ribs are received in one or more corresponding grooves formed in the apparatus.

In accordance with an embodiment of the present invention the closure member includes a hub, wherein when the door is fully closed, the hub is fixedly received in a snap member.

BRIEF DESCRIPTION OF THE SEVERAL VIEWS OF THE DRAWINGS

The present invention will be understood and appreciated more fully from the following detailed description taken in conjunction with the drawings in which.

DETAILED DESCRIPTION OF THE INVENTION

Figure 1:
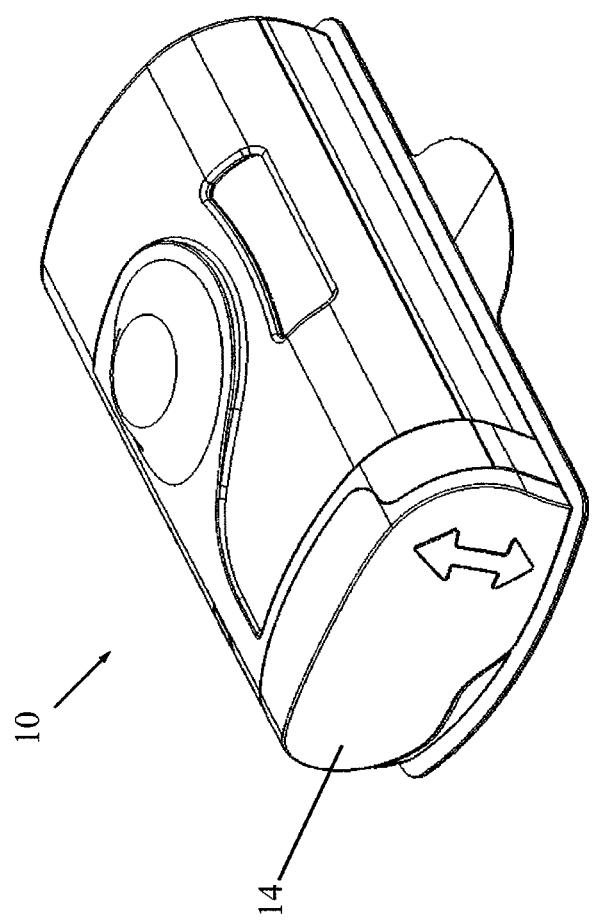
FIG. 1 is a simplified illustration of apparatus for administering a substance to a subject, in accordance with an embodiment of the present invention.
Figure 2:
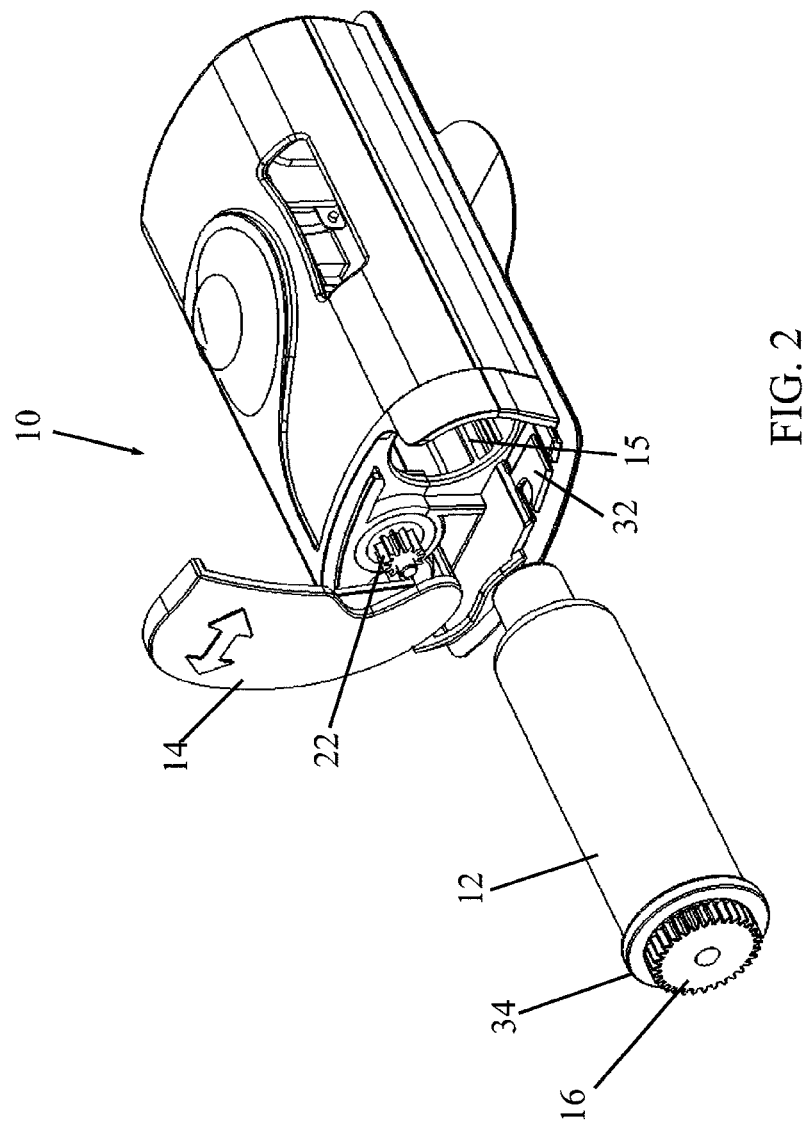
FIG. 2 is a simplified illustration of the apparatus of FIG. 1, showing a door of a cartridge insertion assembly in the open position and a cartridge poised for insertion into the apparatus.

Reference is now made to FIGS. 1 and 2, which illustrate apparatus 10 for administering a substance (e.g., insulin) to a subject, in accordance with a non-limiting embodiment of the present invention. Typically, apparatus 10 includes a cartridge 12 (FIG. 2) that contains the substance to be administered to a subject. FIG. 2 illustrates a door 14 of a cartridge insertion assembly in the open position and cartridge 12 poised for insertion into a pathway 15 in apparatus 10.

As seen in FIG. 2, cartridge 12 includes a cartridge coupling element 16 (e.g., a gear) for coupling (e.g., meshing) with an activation mechanism 18 (seen in FIG. 4, which typically includes a motor, a battery and a control unit) that causes the substance contained in cartridge 12 to be metered out of cartridge 12 for eventual administration to the patient. (In some embodiments, cartridge coupling element 16 is assembled to an end of a driving screw.) The way in which the activation mechanism works to meter the substance out of cartridge 12 is not pertinent to this invention. By way of example, the activation mechanism may work as in an external drug pump of the type described in US Patent Applications 20090093792 and 20090093793 or PCT Patent Application PCT/IL2008/001312 (published as WO 2009/044401), the disclosures of which are incorporated herein by reference. However, the invention is not limited to such a drug pump, and may be used for any kind of suitable administration of substances, not just by needle puncture into the patient, but also transdermally (wherein the substance is metered by apparatus 10 to a transdermal patch), by spray (wherein the substance is metered by apparatus 10 to a spray nozzle), micro needles array and others.

It is noted that although cartridge 12 is typically a one-use item, the electronics, batteries and motor and other elements of the system can be used more than once if desired.

Figure 3:
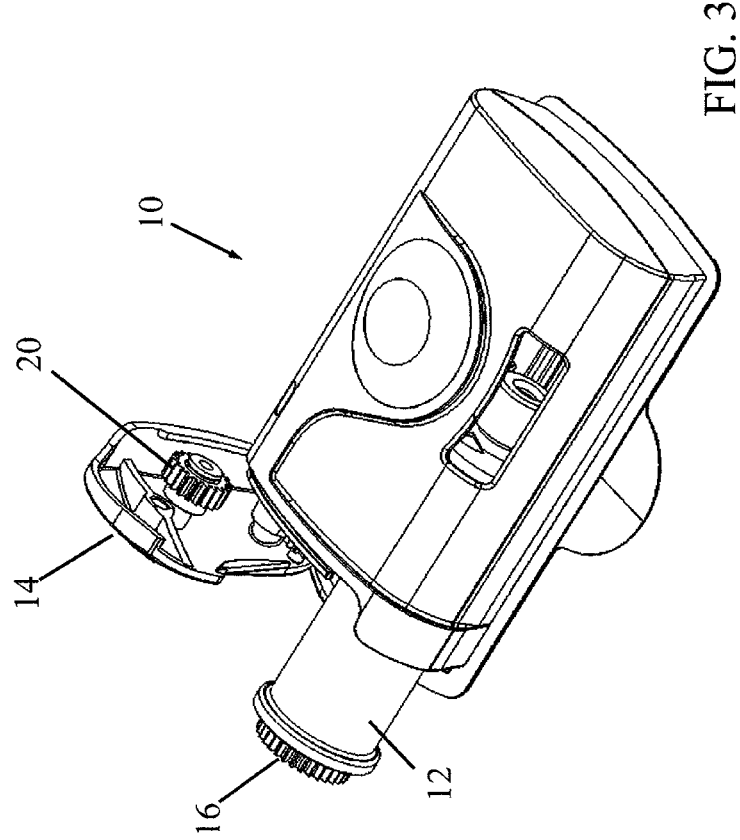
FIG. 3 is a simplified illustration of the cartridge partially inserted into the apparatus.

As seen in FIG. 3, in accordance with a non-limiting embodiment of the present invention, door 14 includes a door coupling element 20 (e.g., a gear, but could also be any other coupling element for transmitting rotary motion, such as a friction wheel) for effecting coupling (e.g., meshing) between the cartridge coupling element 16 and a coupling element 22 (FIG. 2) of the activation mechanism 18, as will be described more in detail below.

Figure 4:
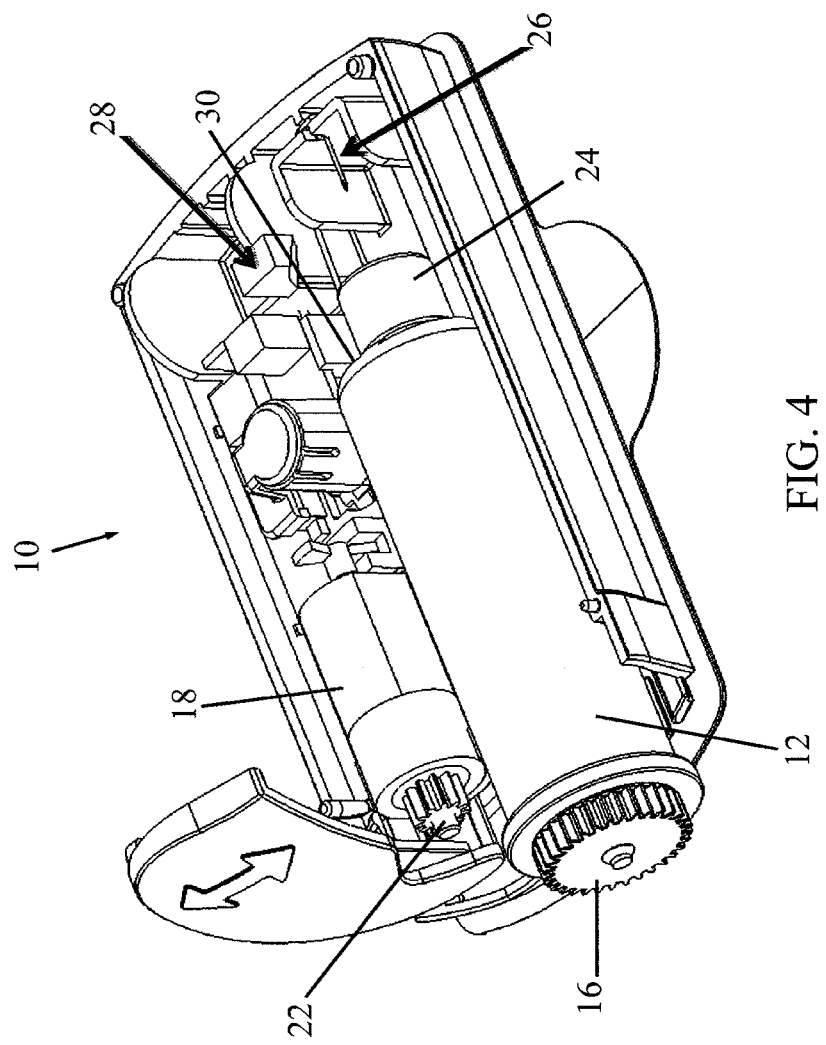
FIG. 4 is a simplified illustration of the cartridge partially inserted into the apparatus, showing components of the cartridge insertion assembly.
Figure 5:
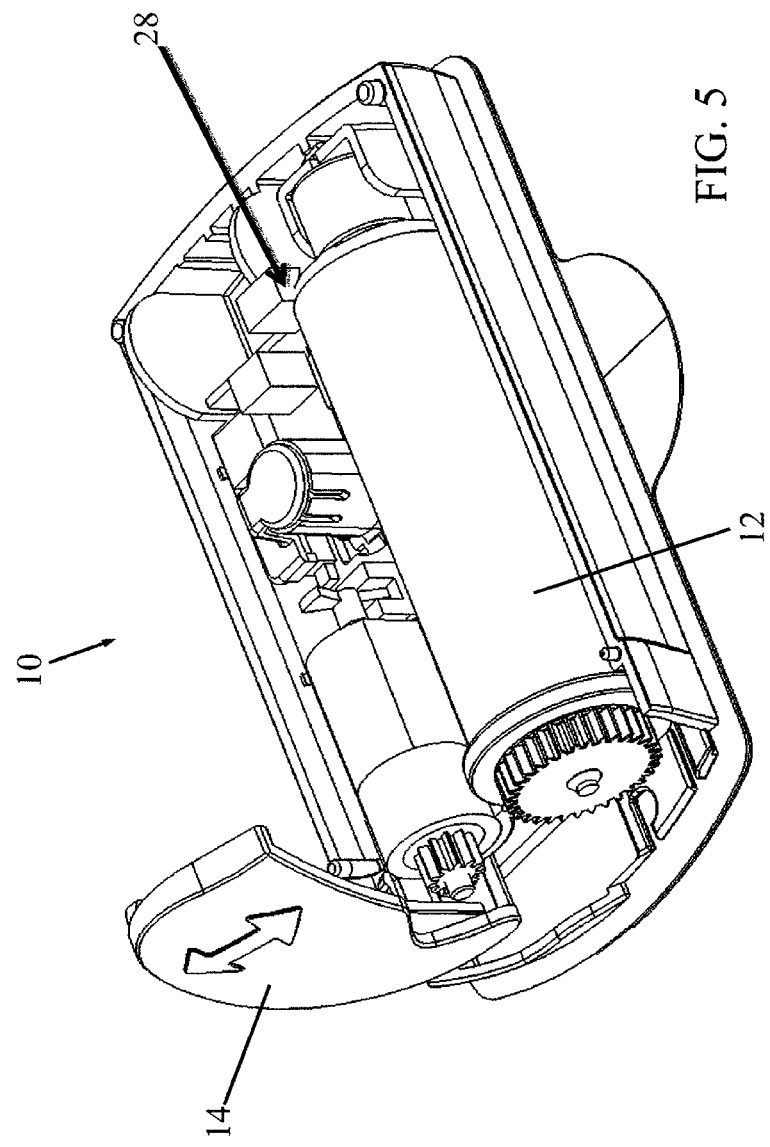
FIG. 5 is a simplified illustration of the cartridge fully inserted into the apparatus up to a cartridge stopper of the cartridge insertion assembly, with the door still open.

Reference is now made to FIG. 4, which illustrates the cartridge 12 partially inserted into apparatus 10, showing components of the cartridge insertion assembly. Cartridge 12 has a septum 24 at an end opposite to cartridge coupling element 16. The septum 24 is pierced by a hollow needle 26 so that contents of cartridge 12 flow out of cartridge 12 into needle 26 and from needle 26 to an exit port (not shown) for eventual administration to the patient. A cartridge stopper 28, which may be made of a rigid material (e.g., plastic) or more preferably a resilient material (e.g., an elastomer or silicone), is provided for arresting movement of cartridge 12 during insertion into apparatus 10 and preventing over-insertion of cartridge 12. Cartridge stopper 28 also prevents the torque, which is generated by the activation mechanism 18 to rotate the driving screw of the cartridge, from rotating cartridge 12. The cartridge stopper 28 abuts against a shoulder 30 of cartridge 12. FIG. 5 shows cartridge 12 fully inserted into apparatus 10 up to cartridge stopper 28 with door 14 still open.

Figure 6:
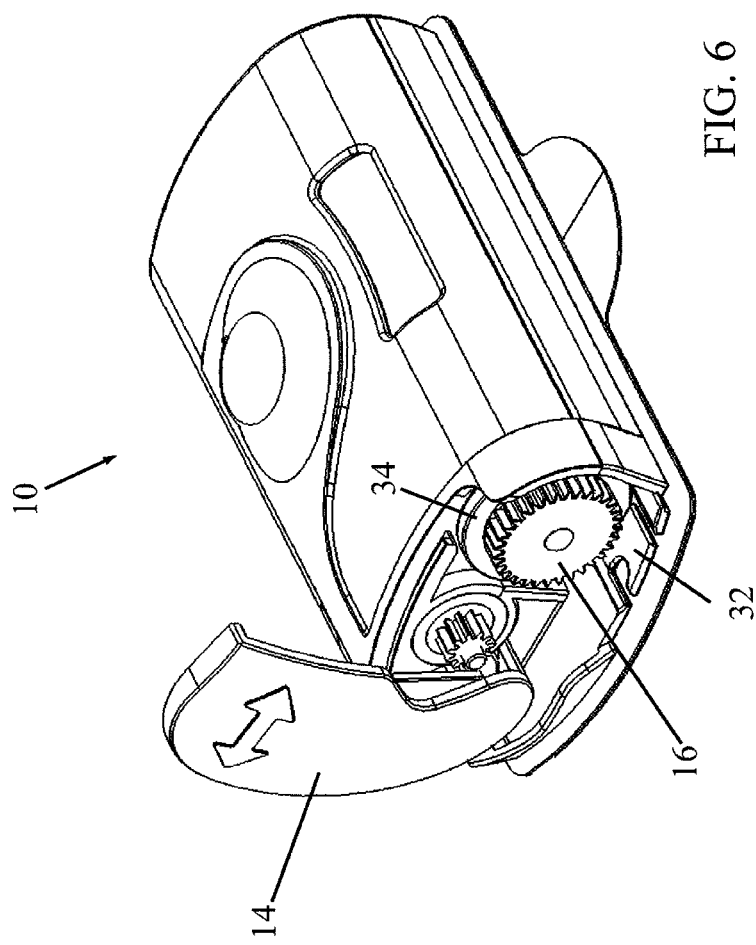
FIG. 6 is a simplified illustration of the cartridge fully inserted into the apparatus and locked in place.
Figure 7:
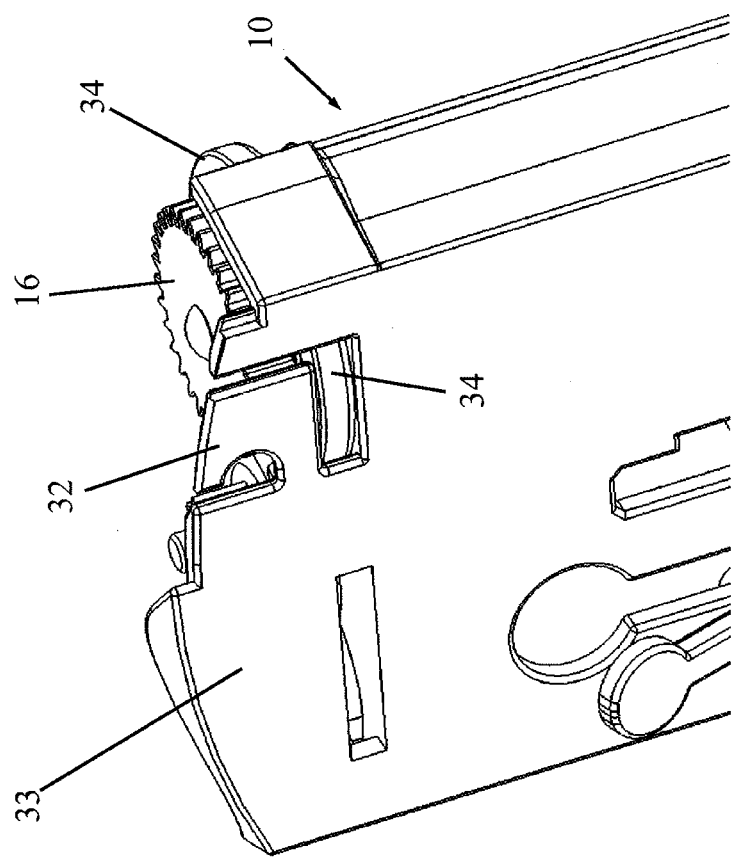
FIG. 7 is a simplified illustration of a locking latch that locks the cartridge in place.

Reference is now made to FIGS. 6 and 7. The cartridge insertion assembly of apparatus 10 includes a locking latch 32 which is cantilevered from a base 33 (FIG. 7) of the apparatus 10. While inserting cartridge 12 into apparatus 10, a rim 34 near cartridge coupling element 16 depresses and slides over locking latch 32. When cartridge 12 is fully inserted into apparatus 10, rim 34 moves past locking latch 32 and locking latch 32 springs back and abuts against rim 34, thereby locking cartridge 12 in place. The user cannot remove cartridge 12 from apparatus 10.

Figure 8:
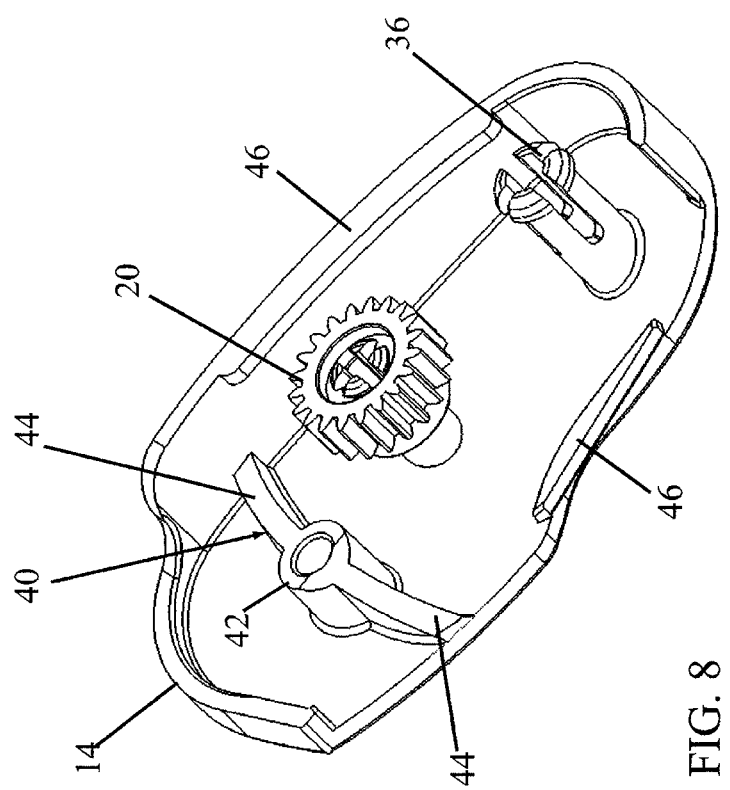
FIG. 8 is a simplified illustration of the inside of the door of the cartridge insertion assembly.
Figure 9:
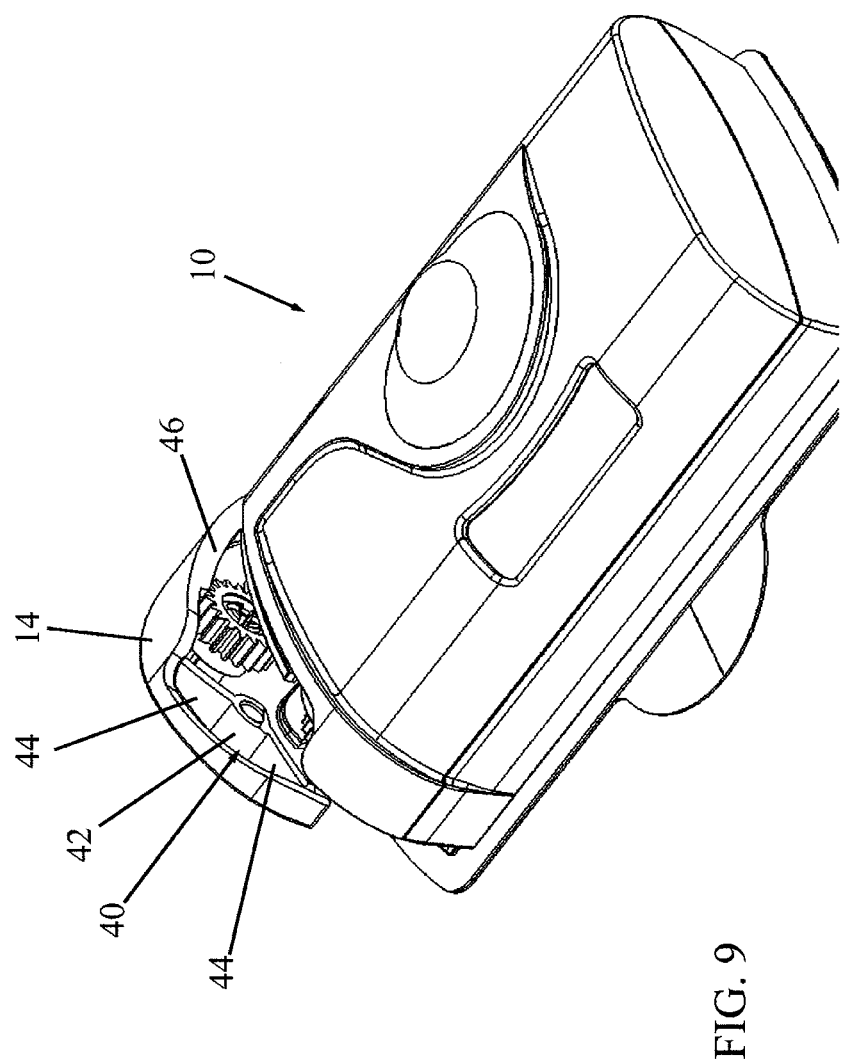
FIG. 9 is a simplified illustration of partially closing the door of the cartridge insertion assembly.

Reference is now made to FIG. 8, which illustrates the inside of door 14. The door coupling element 20 mentioned above is in the middle of the inside of door 14. On one side of element 20 is a hinge member 36 that pivotally connects (e.g., by snap fit) into a corresponding socket 38 (seen in FIG. 10) in the body of apparatus 10. On the other side of element 20 is a closure member 40, which is formed with a central hub 42 and one or more ramp members 44 (in the illustrated embodiment, two inclined ramp members 44 extend on either side of hub 42). Even if the user has not fully inserted cartridge 12 into apparatus 10, the act of closing door 14 (see FIG. 9) causes the ramp members 44 to slide and swipe against cartridge coupling element 16. The inclined surfaces of ramp members 44 gently push and wedge cartridge coupling element 16 to seat fully into apparatus 10 so that septum 24 is pierced by hollow needle 26 as described above with reference to FIGS. 4 and 5.

After the cartridge 12 is locked in place, ramp members 44 keep pushing against the driving screw to create priming of the drug pump, wherein contents of the cartridge 12 overflow and pressurize into the needle 26 and drip out therefrom. This priming process reduces the breaking force (the initial force to remove the plunger after a long storage time) and removes air bubbles from the fluid path.

The inside of door 14 is formed with one or more ribs 46, which when door 14 is fully closed, are received in one or more corresponding grooves 38 (FIG. 10) formed at the end of the housing of apparatus 10. Ribs 46 seated in grooves 48 provide resistance to axial pull-out forces that may be acting on cartridge 12 and door 14 during operation of apparatus 10.

Figure 10:
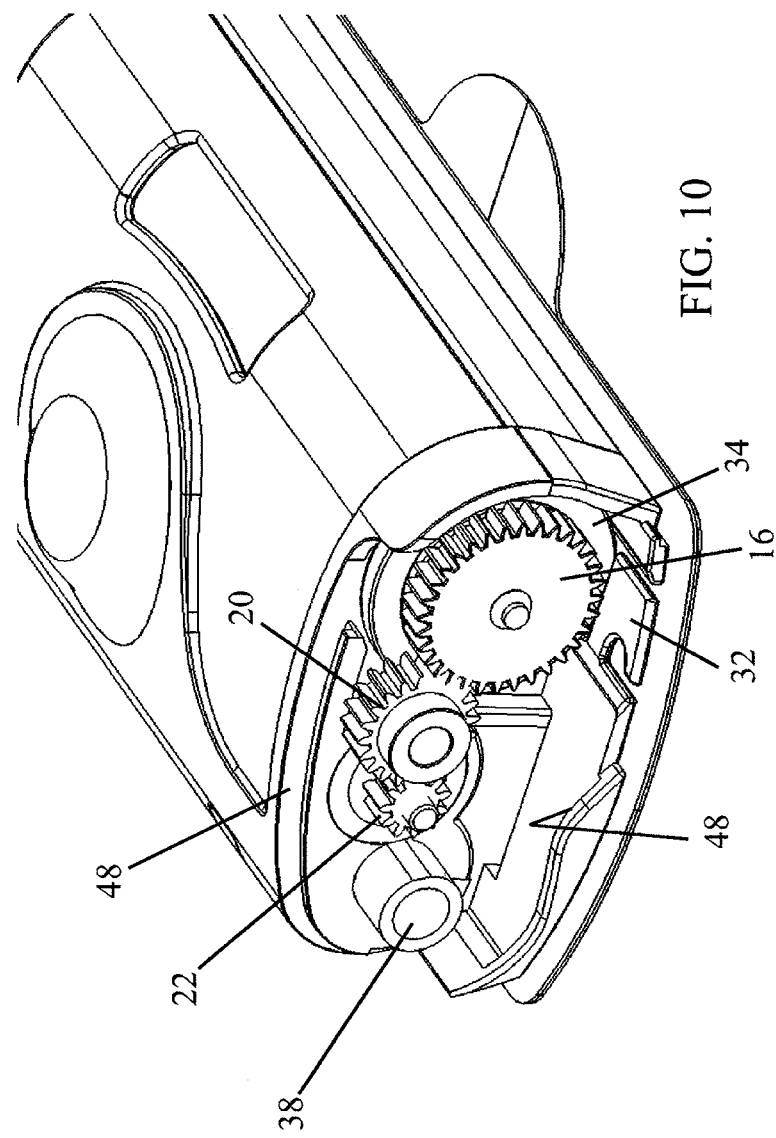
FIG. 10 is a simplified illustration of the door fully closed, but only showing the inner components of the door (e.g., coupling elements) and not the outside surface of the door itself.

FIG. 10 illustrates door 14 fully closed. Door coupling element 20 couples between cartridge coupling element 16 of the cartridge and coupling element 22 of the activation mechanism, so that the activation mechanism can now cause the substance contained in the cartridge to be metered out of the cartridge for eventual administration to the patient.

Figure 11:
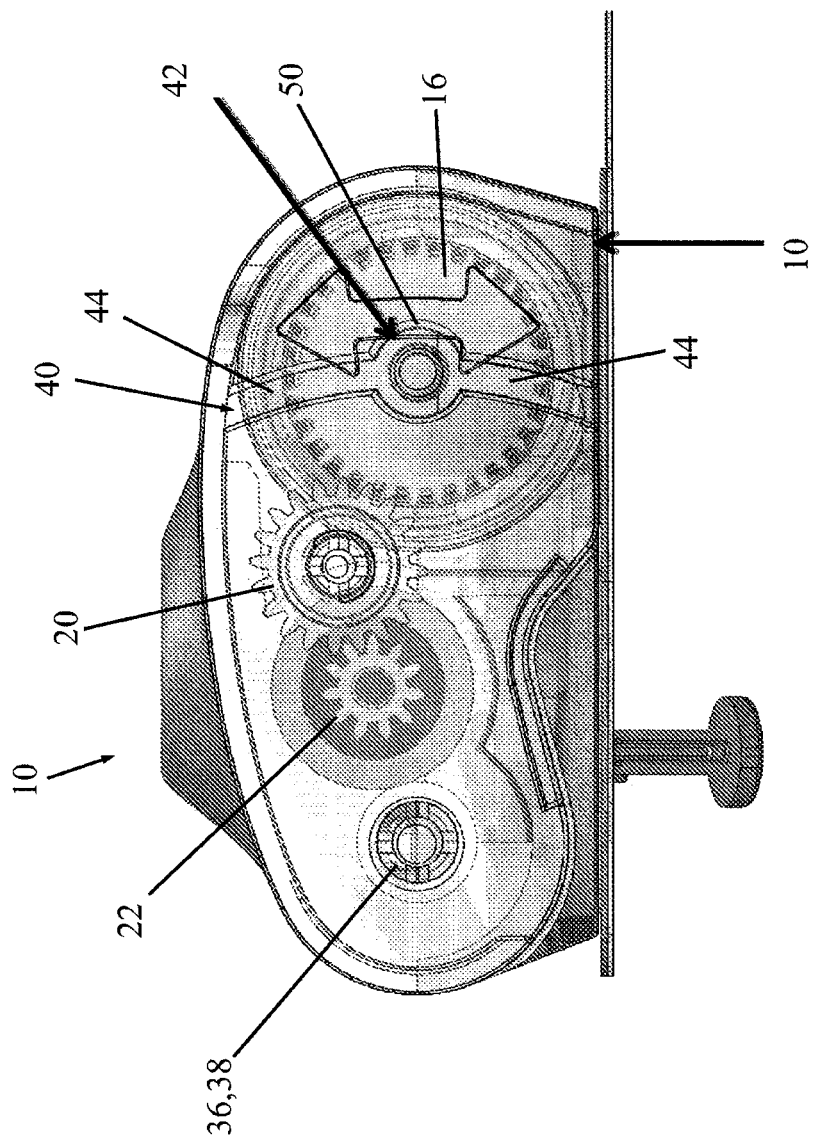
FIG. 11 is a simplified illustration of the door fully closed, showing a snap that snaps the door to the body of the apparatus.

Reference is now made to FIG. 11. When door 14 is fully closed, hub 42 of closure member 40 snaps and is fixedly received in a snap member 50 (curved snap member) so that door 14 is properly secured to the body of apparatus 10.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

I claim:

1. A cartridge insertion assembly comprising:
   an apparatus with a pathway formed therein;
   a cartridge insertable into said pathway, said cartridge comprising a cartridge coupling element connectable to an activation mechanism disposed in said apparatus operative to cause a substance contained in said cartridge to be metered out of said cartridge; and
   a door pivoted to said apparatus that comprises a door coupling element arranged with respect to said cartridge such that when said door is in a fully closed position, said door coupling element couples said cartridge coupling element with a coupling element of said activation mechanism.

2. The cartridge insertion assembly according to claim 1, further comprising a locking latch cantilevered from a base of said apparatus, wherein when said cartridge is fully inserted in said apparatus, said locking latch abuts against a rim of said cartridge, thereby locking said cartridge in said pathway.

3. The cartridge insertion assembly according to claim 1, wherein when said cartridge is fully inserted in said apparatus, said cartridge abuts against a cartridge stopper disposed in said apparatus.

4. The cartridge insertion assembly according to claim 1, wherein said cartridge comprises a septum at an end opposite to said cartridge coupling element, and said apparatus comprises a hollow needle, wherein when said cartridge is fully inserted in said apparatus, said needle punctures said septum.

5. The cartridge insertion assembly according to claim 1, wherein said door comprises a closure member on an inside surface thereof, said closure member comprising one or more inclined ramp members, wherein closing said door causes said ramp members to slide and push against said cartridge coupling element so as to push said cartridge fully into said apparatus.

6. The cartridge insertion assembly according to claim 1, wherein said door is formed with one or more ribs, which when said door is fully closed, said ribs are received in one or more corresponding grooves formed in said apparatus.

7. The cartridge insertion assembly according to claim 1, wherein said door comprises a closure member on an inside surface thereof, said closure member comprising a hub, wherein when said door is fully closed, said hub is fixedly received in a snap member.

8. The cartridge insertion assembly according to claim 1, wherein said coupling elements comprise gears.

9. A cartridge insertion assembly comprising:
   apparatus with a pathway formed therein;
   a cartridge insertable into said pathway, said cartridge comprising a cartridge coupling element connectable to an activation mechanism disposed in said apparatus operative to cause a substance contained in said cartridge to be metered out of said cartridge; and
   a door pivoted to said apparatus that comprises a door coupling element sized and shaped to transmit rotary motion, said door coupling element being arranged with respect to said cartridge such that when said door is in a fully closed position, said door coupling element couples said cartridge coupling element with a coupling element of said activation mechanism.

10. The cartridge insertion assembly according to claim 9, further comprising a locking latch cantilevered from a base of said apparatus, wherein when said cartridge is fully inserted in said apparatus, said locking latch abuts against a rim of said cartridge, thereby locking said cartridge in said pathway.

11. The cartridge insertion assembly according to claim 9, wherein when said cartridge is fully inserted in said apparatus, said cartridge abuts against a cartridge stopper disposed in said apparatus.

12. The cartridge insertion assembly according to claim 9, wherein said cartridge comprises a septum at an end opposite to said cartridge coupling element, and said apparatus comprises a hollow needle, wherein when said cartridge is fully inserted in said apparatus, said needle punctures said septum.

13. The cartridge insertion assembly according to claim 9, wherein said door comprises a closure member on an inside surface thereof, said closure member comprising one or more inclined ramp members, wherein closing said door causes said ramp members to slide and push against said cartridge coupling element so as to push said cartridge fully into said apparatus.

14. The cartridge insertion assembly according to claim 9, wherein said door is formed with one or more ribs, which when said door is fully closed, said ribs are received in one or more corresponding grooves formed in said apparatus.

15. The cartridge insertion assembly according to claim 9, wherein said door comprises a closure member on an inside surface thereof, said closure member comprising a hub, wherein when said door is fully closed, said hub is fixedly received in a snap member.

16. The cartridge insertion assembly according to claim 9, wherein said coupling elements comprise gears.

17. A cartridge insertion assembly comprising:
   an apparatus with a pathway formed therein;
   a cartridge insertable into said pathway, said cartridge comprising a cartridge coupling element connectable to an activation mechanism disposed in said apparatus operative to cause a substance contained in said cartridge to be metered out of said cartridge;
   a door pivoted to said apparatus that comprises a door coupling element arranged with respect to said cartridge such that when said door is in a fully closed position, said door coupling element couples said cartridge coupling element with a coupling element of said activation mechanism; and
   a locking latch cantilevered from a base of said apparatus, wherein when said cartridge is fully inserted in said apparatus, said locking latch abuts against a rim of said cartridge, thereby locking said cartridge in said pathway, and wherein when said cartridge is fully inserted in said apparatus, said cartridge abuts against a cartridge stopper disposed in said apparatus.

* * * * *